United States Patent [19]
Rahman

[11] Patent Number: 6,146,659
[45] Date of Patent: *Nov. 14, 2000

[54] METHOD OF ADMINISTERING LIPOSOMAL ENCAPSULATED TAXANE

[75] Inventor: Aquilur Rahman, Long Grove, Ill.

[73] Assignee: Neopharm, Inc., Bannockburn, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 09/108,509

[22] Filed: Jul. 1, 1998

[51] Int. Cl.$^7$ ..................................... A61K 9/127
[52] U.S. Cl. ........................ 424/450; 514/449; 514/510
[58] Field of Search ........................... 424/450; 514/449, 514/510

[56] References Cited

U.S. PATENT DOCUMENTS

| | | | |
|---|---|---|---|
| 5,424,073 | 6/1995 | Rahman | 424/450 |
| 5,648,090 | 7/1997 | Rahman | 424/450 |
| 5,683,715 | 11/1997 | Boni | 424/450 |
| 5,756,537 | 5/1998 | Gill | 514/449 |

OTHER PUBLICATIONS

'Liposomes' Ed. by Ostro, Marcel Dekker, Inc. pp. 277–337, 1987.

Bonadonna, Annals of Oncology, 3, pp. 419–421, 1992.

*Primary Examiner*—Gollamudi S. Kishore
*Attorney, Agent, or Firm*—Leydig, Voit & Mayer, Ltd.

[57] ABSTRACT

Liposomal-encapsulated taxane or an antineoplastic derivative thereof or a mixture thereof is provided which is used to effect a therapeutically enhanced method of treating cancer. The liposomal encapsulated paclitaxel allows for administration to a patient in less than one hour.

15 Claims, No Drawings

METHOD OF ADMINISTERING LIPOSOMAL ENCAPSULATED TAXANE

TECHNICAL FIELD OF THE INVENTION

The present invention relates to a method of administering a liposomal encapsulated taxane.

BACKGROUND OF THE INVENTION

The use of taxanes, such as paclitaxel, as antitumor agents for patients suffering from diseases such as ovarian and breast cancer, is known. In addition, paclitaxel has been shown to be clinically potent as a synergistic agent when used in conjunction with radiation treatment. Paclitaxel has a unique mechanism of action and a broad spectrum of anticancer activity because paclitaxel shows stabilization of microtubules rather than disassembly of microtubules.

However, paclitaxel has extremely low solubility in water, which makes it difficult to provide a suitable dosage form. Currently, paclitaxel is prepared and administered in a vehicle containing Cremophor EL (a polyethoxylated castor oil) and ethanol in a 50:50 (vol/vol) ratio. This solution is diluted 1:10 in saline before being administered to humans. The stability of paclitaxel once diluted in saline solution is quite low. The drug degrades within 24 hours and, thus, handling of dosage for the patients becomes very difficult. Since, the drug precipitates from dilution, an on-line filter is utilized for the infusion of the drug to the patients.

In clinical trials, a consistent problem of anaphylactoid reaction, dyspnea, hypertension, and flushing have been encountered. The dose-limiting toxicity is myelosuppression and due to the cardiac toxicity of the present paclitaxel the patient must be hospitalized for continuous infusion of the drug.

Attempts to prevent paclitaxel cardiotoxicity and anaphylactoid reaction have included reliance on pretreatment of patients with antihistamine and corticosteroids, and by prolonging the infusion time from six to twenty four hours. U.S. Pat. No. 5,621,001 (Canetta et al.) discloses a prolonged infusion time in a method for reducing peripheral neurotoxicity symptoms while maintaining an anti-tumor effect in patients suffering from ovarian cancer and undergoing paclitaxel therapy. This method involves administering about 135 mg/m$^2$ of paclitaxel over a period of about 24 hours. The administration of paclitaxel is repeated at least once, about 21 days after the preceding administration.

U.S. Pat. No. 5,665,761 (Canetta et al.) discloses a pretreatment stage before administration of paclitaxel. The '761 patent provides for paclitaxel infusions over a duration of less than six hours, preferably about three hours, utilizing dosages of between about 135 mg/m$^2$ and about 275 mg/m$^2$, preferably between about 135 mg/m$^2$ and about 175 mg/m$^2$, after patients had been pretreated to alleviate or minimize hypersensitivity responses. For example, the patients are pre-medicated with steroids, antihistamines, and H$_2$-antagonists sufficient to at least prevent an anaphylactoid shock capable of causing acute hypersensitivity reactions and patient death. U.S. Pat. No. 5,670,537 (Canetta et al.) also discloses this method of administration for a patient suffering from a paclitaxel-sensitive tumor, such as an ovarian tumor.

U.S. Pat. No. 5,641,803, discloses the administration of paclitaxel to a patient, wherein about 135–175 mg/m$^2$ of paclitaxel is administered over a period of about three hours. Such a period purportedly was used to overcome, in part, some of the aforementioned problems associated with short infusion times, such as one hour, which had been employed with the conventional paclitaxel formulations containing polyethoxylated castor oil.

In yet another attempt to address the toxicity concerns of the conventional paclitaxel formulation, U.S. Pat. No. 5,696,153 suggests the use of an administration regimen wherein 45 to 120 mg/m$^2$ of paclitaxel is administered over a period of 60 to 180 minutes, a plurality of times during a 21 day period, with each infusion being separated by an interval of between 4 to 5 days.

However, even with these manipulations of prolonged infusion time and pretreatment of patients with antihistamines and corticosteroids, the patients suffer from serious toxicities which are often fatal. Different agent delivery systems are being utilized to enhance tumor cell-fighting effects of the drug and/or reduce systemic toxicity. Liposomes are one of many carriers that have been developed to help anti-tumor agents become more efficient and less toxic. A "liposome" is a closed structure composed of lipid bi-layers surrounding an internal aqueous space.

U.S. Pat. No. 5,648,090 (Rahman et al.) and U.S. Pat. No. 5,424,073 (Rahman et al.) provide a liposomal encapsulated paclitaxel for a method for treating cancer in mammals using such a liposomal-encapsulated paclitaxel, or anti-neoplastic derivative thereof. The '090 and '073 patents disclose a method of modulating multidrug resistance in cancer cells in a mammalian host by administering to the host a pharmaceutical composition of a therapeutically effective number of liposomes which include a liposome-forming material, cardiolipin, and an agent such as paclitaxel, or an antineoplastic derivative of paclitaxel, or a mixture thereof; and a pharmaceutically acceptable excipient.

Up until the present invention the fastest administration time tolerated by most patients was optimally a three hour time period. However, there is still a need for a more rapid and less toxic method of administration of paclitaxel. The present invention provides such a method.

SUMMARY OF THE INVENTION

The present invention provides a method of administering a taxane to a patient by administering taxane over a period of less than an hour in an amount from about 75 to 300 mg/m$^2$ wherein the taxane is a liposomal encapsulated taxane or an antineoplastic derivative thereof. The method does not require premedication, as with anti-hypersensitivity agents.

The present invention provides a method of administering a liposomal encapsulated taxane or an antineoplastic derivative thereof, which minimizes the duration of administration and minimizes the accompanying side effects. It is also an object of the present invention to provide a method for treating cancer.

These and other advantages of the present invention, as well as additional inventive features, will be apparent from the description of the invention provided herein.

The invention may best be understood with reference to the following detailed description of the preferred embodiments.

DESCRIPTION OF THE PREFERRED EMBODIMENTS

The present invention provides a method of administering a taxane to a patient in need of treatment with a taxane. In part, the present invention provides a delivery system for a taxane to a host which is characterized by the avoidance of solubility problems of a taxane; the improved taxane stability; the avoidance of anaphylactoid reactions and cardiotoxicity; the ability to administer a taxane as a bolus or short infusion, rather than an extended (24-hour) infusion of free taxane; the increased therapeutic efficacy of taxane; and the modulation of multidrug resistance in cancer cells.

The taxane is delivered in the form of a liposomal encapsulated taxane or antineoplastic derivative thereof. Preferably, the taxane is paclitaxel. A suitable derivative of paclitaxel is taxasm. Other suitable taxanes are 7-epipaclitaxel, t-acetyl paclitaxel, 10-desacetyl-paclitaxel, 10-desacetyl-7-epipaclitaxel, 7-xylosylpaclitaxel, 10-desacetyl-7-glutarylpaclitaxel, 7-N,N-dimethylglycylpaclitaxel, 7-L-alanylpaclitaxel, taxotere, and mixtures thereof.

The pharmaceutical composition may also include a cardiolipin. The cardiolipin may be obtained from either a natural or synthetic source. The taxane, such as paclitaxel, is encapsulated in liposomes using the cardiolipin. In addition to cardiolipin, the taxane may be encapsulated in liposomes using phosphatidylcholine and cholesterol. Such a composition of lipids provides over 90% encapsulation of the drug in liposomes.

The liposomal encapsulated taxane is prepared by various processes. For example, the taxane or a derivative thereof is dissolved in a solvent. Any nonpolar or slightly polar solvent may be used. Suitable solvents include t-butanol, ethanol, methanol, chloroform or acetone. Then, cardiolipin is dissolved in a suitable solvent as described for taxane. The taxane and the cardiolipin solutions are then mixed. Then, lipid-forming material is dissolved in a suitable solvent, which is generally a low polarity solvent such as a t-butanol, chloroform, or a non-polar solvent, such as n-hexane. The solvent mixture containing the taxane and the cardiolipin and the solution containing the lipid-forming material are mixed, and the solvents are removed, as by lyophilization to afford a dry lipid and drug. Liposomes are then formed by adding saline solution thereto. Thereafter, multilamellar liposomes may be formed by mixing the liposomes, for example, as by vortexing.

The liposome is a closed structure composed of lipid bilayers surrounding an internal aqueous space. Generally, the liposomes may be neutral, negative or positive liposomes. For example, positive liposomes may be formed from a solution containing phosphatidyl choline, cholesterol, and stearyl amine. Negative liposomes may be formed, for example, from solutions containing phosphatidyl choline, cholesterol, cardiolipin and phosphatidyl serine. The liposomes can be a mixture of multilamellar vesicles and unilamellar vesicles. Storage temperature and pH can vary. For example, the liposomal encapsulated paclitaxel is preferably stored at about −20° C. and suspensions of the pharmaceutical composition of the present invention in buffered, neutral pH saline are stable for periods of only hours up to months, depending upon the temperature, paclitaxel content, and phospholipid constituents.

The liposomal drug delivery system which features a high drug to carrier ratio can alter drug pharmacokinetics, maintaining the plasma concentration of the drug at an increased level over a longer period of time. The biodegradability and the low inherent toxicity and immunogenicity of liposomal preparations allows diminished toxicity with respect to free-floating agents in the plasma.

These liposomes used as a drug-delivery system, afford a high concentration and/or long duration of action at a target site, where beneficial effects may occur while maintaining a low concentration and/or reduced duration at other sites, where adverse effects may occur. For example, encapsulation of paclitaxel provides higher peak plasma concentrations, longer presence of the drug in the body, and higher AUC than the conventional paclitaxel.

The present pharmaceutical composition is administered in the amount of about 50 to 300 mg active compound/m$^2$ of mammalian host surface area. For a human, for example, of about 70 kg body weight, from about 0.5 to 5.0 mg active compound per kg of body weight is administered. Preferably, about 1.0–3.0 mg of active compound per kg of body weight is administered. Preferable amounts include 75, 135, 175, 250, and 300 mg/m$^2$.

Liposomal encapsulated taxane has substantial beneficial effect in overcoming multidrug resistance in cancer cells which are subjected to chemotherapy. By using the liposomal composition of the present invention, it is possible to reduce the tendency of cancer cells subjected to chemotherapy to develop resistance to the chemotherapeutic agents used for chemotherapy such as anthracycline glycosides. This method includes administering to a host a pharmaceutical composition of a liposomal encapsulated taxane of the present invention in accordance with the administration protocol.

Taxanes and the anti-neoplastic derivatives thereof may be used to treat any form of mammalian cancer. Such compounds may function by promoting the assembly of microtubules or prohibiting the tubulin disassembly process. Taxane and the anti-neoplastic derivatives thereof are particularly advantageous in treating mammalian lymphoma, ovarian, breast, lung and colon cancer, and particularly those conditions in humans.

The present liposome compositions can be administered intravenously or intraperitoneally to an isolated portion of a mammalian body particularly a human body, such as an arm or leg, or in the case of a human, a hand.

The following examples further illustrate the present invention but, of course, should not be construed as in any way limiting its scope.

EXAMPLE 1

Paclitaxel is encapsulated in liposomes using cardiolipin, phosphatidylcholine, cholesterol and -tocopherol. This composition of lipids provides over 90% encapsulation of the drug in liposomes. The paclitaxel in liposomal formulation is stable for days at room temperature and at −20° C. for at least 5 months. No degradation or precipitation of paclitaxel is observed at any storage temperature and appears to be ideally suited for systemic administration in accordance with the present invention.

The proportion of lipids per mg of paclitaxel is:

1.8 mg cardiolipin
9.0 mg phophatidylcholine
3.0 mg cholesterol
0.1 mg -tocopherol The liposome encapsulated paclitaxel is manufactured using the following procedure.

8.89 kilograms of t-butyl alcohol are added to a 12.0 liter flask and heated to 40–45 degrees C. The following additions are made with mixing until dissolution and heating at 40–45 degrees. 3.412 grams of D-alpha-tocopheryl acid succinate are then added followed by 205 grams of egg phosphatidylcholine. 22.78 grams of paclitaxel are then added, followed by 41.00 grams of tetramyristoyl cardiolipin. 68.33 grams of cholesterol are then added and the resulting solution filtered through a 0.22 micron filter.

The resulting filtrate is filled into sterile vials, each containing about 10.1 grams of filtrate. The vials are stoppered and subjected to lyophilization.

After lyophilization the vials are reconstituted, as needed, with 25 ml of normal saline, are vortexed for about 2 minutes and allowed to hydrate at room temperature for about 30 minutes, after which time the vials are sonicated for about 5–10 minutes in a bath type sonicator at maximum frequency. The content of the vial is then transferred to an infusion bag and used in accordance with the present invention.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A method of administering taxane to a human patient in need of treatment with taxane comprising administering to the human patient a pharmaceutical composition over a period of less than an hour in an amount from about 75 to 300 mg/m$^2$ wherein said pharmaceutical composition is liposomal encapsulated paclitaxel.

2. The method of claim 1 wherein said pharmaceutical composition further comprises a pharmaceutically acceptable excipient.

3. The method of claim 1 wherein said pharmaceutical composition further comprises cardiolipin.

4. The method of claim 3 wherein said cardiolipin is selected from the group consisting of natural cardiolipin and synthetic cardiolipin.

5. The method of claim 1 wherein said amount of said paclitaxel is about 75 mg/m$^2$.

6. The method of claim 1 wherein said amount of said paclitaxel is about 135 mg/m$^2$.

7. The method of claim 1 wherein said amount of said paclitaxel is about 175 mg/m$^2$.

8. The method of claim 1 wherein said amount of said paclitaxel is about 250 mg/m$^2$.

9. The method of claim 1 wherein said amount of said paclitaxel is about 300 mg/m$^2$.

10. The method of claim 1 wherein said patient is suffering from an ovarian cancer, breast cancer, or lung cancer.

11. The method of claim 1 wherein said liposomal encapsulated paclitaxel is administered by intravenous infusion.

12. The method of claim 11 wherein said liposomal encapsulated paclitaxel is administered over a period of 45 minutes.

13. The method of claim 11 wherein said administration of said liposomal encapsulated paclitaxel is repeated at least once every 21 days.

14. The method of claim 1 wherein said administration of said liposome encapsulated paclitaxel is administered intraperitoneally to patients suffering from cancer.

15. The method of claim 14 wherein said administration of said liposome encapsulated paclitaxel is administered intraperitoneally to patients suffering from colon cancer.

* * * * *